United States Patent [19]

Müller et al.

[11] Patent Number: 4,608,983
[45] Date of Patent: Sep. 2, 1986

[54] GENERATION FOR SHOCK WAVES FOR CONTACTLESS DESTRUCTION OF CONCREMENTS IN A LIVING BEING

[75] Inventors: Hans G. Müller, Friedrichshafen; Othmar Wess, Immenstaad, both of Fed. Rep. of Germany

[73] Assignee: Dornier System GmbH, Friedrichshafen, Fed. Rep. of Germany

[21] Appl. No.: 604,859

[22] Filed: Apr. 27, 1984

[30] Foreign Application Priority Data

May 7, 1983 [DE] Fed. Rep. of Germany ....... 3316837

[51] Int. Cl.$^4$ ............................................ A61B 17/22
[52] U.S. Cl. .................................................. 128/328
[58] Field of Search ..................... 128/328, 24 A, 804; 604/22; 367/138; 313/113

[56] References Cited

FOREIGN PATENT DOCUMENTS 2635635 5/1979 Fed. Rep. of Germany ...... 128/328
3146626 6/1983 Fed. Rep. of Germany ...... 128/328

Primary Examiner—Michael H. Thaler
Attorney, Agent, or Firm—Ralf H. Siegemund

[57] ABSTRACT

The apparatus includes an ellipsoidal reflection chamber having two focal points, one to be aligned with the concrement to be destroyed, the other one being located in a discharge path between two electrodes facing each other and being oriented in the longitudinal axis of the ellipsoid; one of the electrodes is a point-like extension of an inner one of two coaxial conductors, and the outer one of these conductors carries several flat arch shaped holders positioning the other electrode likewise in said longitudinal axis, the holding structure in the vicinity of the inner conductor continuing the ellipsoidal reflecting surface; through a threaded mount the two electrodes can be moved towards and away from each other; each of these electrodes is preferably provided for easy exchange to compensate burning off.

7 Claims, 3 Drawing Figures

GENERATION FOR SHOCK WAVES FOR CONTACTLESS DESTRUCTION OF CONCREMENTS IN A LIVING BEING

BACKGROUND OF THE INVENTION

The present invention relates to the generation of shock waves by means of a spark and to be used for the contactless destruction of concrements present in the body of a living being.

U.S. Pat. No. 3,942,531 discloses a device for the destruction and breaking up of concrements situated in the body of a livng being, and in particular this patent discloses a focusing chamber in cooperation with a spark and shock wave generator. The focusing chamber provides specifically for the focusing of the shock wave that issues from a spark. The focusing chamber is basically configured as far as geometry is concerned as a rotational ellipsoid having two focal points. The spark and therefore the shock wave is generated in one of these points. If the electric discharge resulting in this spark is carried out under water and is in fact highly concentrated in that one of the focal points of the ellipsoid, one can in fact generate a highly concentrated shock wave in the second focal point of the ellipsoid. In other words, near pointlike focusing is indeed made possible by means of the rotational-ellipsoidal focusing chamber. The amplitude attainable in the second focal point is in excess of 1 kilobar, and a pulse will have a duration less than one microsecond. This then permits the breaking up and destruction of concrements within the body of a living being, the concrement being situated in that second focal point. Indeed such a concrement can be broken up into smaller pieces which can then be extracted or discharged otherwise.

The known equipment includes two electrodes facing each other in the first mentioned focal point of the ellipsoid, but requiring separate electrical conductors. In order to attain a suitably strong shock wave, voltages between 15 and 30 killovolts are necessary. The effective destruction of such a concrement depends essentially on a very steep flank or leading edge of the shock wave pulse produced, and of course on the duration of that pulse. Generally speaking, one can say that the underwater spark generator requires a very high mechanical strength and very particular and critical electrical properties; the design criteria must be met with a very high degree of accuracy.

German Patent 2,635,635 discloses a spark generator for the generation of shock waves for the contact-less destruction of concrements in living beings, whereby specifically the conductors to and from the electrodes have a low inductivity for better control of the timing of the spark to be generated. The electrodes extend from a holder, and one of the electrodes is extended and looped back so that the electrodes face each other axially. This spark gap as such is exchangeable and placed laterally in the reflector. Thus the electrodes are not coaxially arranged on the large axis of the reflector, which means that the overall rotational symmetry as provided by the chamber is interferred with. This in turn means that a certain interference occurs in the regular propagation pattern of the shock waves so that a certain asymmetry can occur in the focusing. The same is true if one of the outer conductors is constructed as a cage upon which is affixed a second electrode.

The U.S. Pat. No. 3,970,076 discloses a device for the generation of shock waves by means of a spark in the main apex of a reflector. Again, however, the electrodes are not placed coaxial to the large or long axis of the reflecting system.

DESCRIPTION OF THE INVENTION

It is an object of the present invention to provide a particular spark generator and discharge path for the generation of shock waves, for purposes of breaking up and destroying concrements in living beings, whereby particularly the pulse length and duration is extremely short and the device is to have a high mechanical strength and converts electrical energy into focused shock waves at a higher degree of efficency that was heretofore possible; particularly, irregular spark paths are to be avoided, and the spark generating discharge path has to be configured so as to obtain the largest possible effective radiating area which in effect is uniform as far as reflective interaction and aereal distribution of interaction with the focusing chamber is concerned.

It is therefore a specific object of the present invention to provide a new and improved discharge path and spark generator for the generation of shock waves in one focal point of an ellipsoidal reflector for purposes of contact free breaking up and destruction of a concrement in a living being and situated in the second focal point of the ellipsoid, under utilization of coaxial inner and outer conductors, whereby the inner conductor tapers to a first electrode and the outer conductor is continued in a cage in which is fastened the second electrode.

In accordance with the preferred embodiment of the present invention, it is suggested to improve an arragement in accordance with a specific object such that the two electrodes are situated on the large or long axis of the ellipsoid geometrically defining the effective surface of the reflector, that the cage is established from radially oriented arch shaped support elements "reaching" around one of the focal points and having a flat cross section, and that the outer conductor is constructed as a shaft end being configured to continue the ellipsoidal reflecting and focusing surface.

In furtherance of the invention, it is suggested to use thin cylindrical rods as electrodes which are electrically insulated through suitable coating for purposes of protecting them against irregular discharges. These rods should be fastened in an easily exchangeable manner, and they should be configured to be moveable in relation to each other through the simple turning of a sleeve or the like. The shaft end is to be made of a material which reflects shock waves quite well, at least when incident in normal direction. Brass is to be the preferred material here.

The invention offers a variety of significant advantages. First of all, upon placing the electrodes on the large axis of the ellipsoid, a higher efficiency as far as shock wave generation and concentration is obtained, because the main direction for radiating shock waves, i.e., the principal transmission lobe extends transversely to the electrodes in rotationally symmetrical undisturbed fashion, which in turn permits a much better and much more uniform reflection. The arches which extend around the focal point avoid irregular discharges. The flat construction of these arches, particularly as far as radial orientation if concerned, insures a high degree of stability. Moreover, these arches have a reduced inductivity which in turn minimizes any interference in the propagation of the shock wave. The spark occurs always in the (focal) center of the reflector, even after a certain burnoff has been observed. The shaft end is matched to the curvature of the reflector and increases therefore the effective reflective area.

The utilizaton of thin rods as electrodes which are coated for purposes of preventing parasitic discharges to an arch is another highly significant detail of the invention. This coating, particularly of the cylindrical surface of the rod, avoids lateral or parasitic discharges from points other than the tip of the rod. The electrodes should be easily exchangeable, and preferably they should also be easily readjustable. If thin rods are used, no sharpening is needed, one can instead use rather inexpensive round thin rods. Since the rods are very thin, they do not interfere in the propagation of the shock waves. The sleevelike adjustment mentioned earlier is primarily provided in order to compensate for any burnoff that may occur on the tips of these rods. This in turn means that the overall life without replacement of the equipment is enchanced. Moreover, once a rod has become unusable, it can be easily be exchanged.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding now to the detailed description of the drawings, FIG. 1 illustrates a focusing chamber 2 having an internal surface 6 which is a portion of a rotational ellipsoid. Hence the illustrated cross section through that chamber wall defines an elliptical wall portion. The ellipsoidal or truncated ellipsoidal chamber is filled with liquid (4). Above the ellipsoid 2 a pan 7 is provided which is likewise filled with liquid. Reference numeral 8 refers to the body of a living being having in one of the organs a concrement 9 such as a kidney stone. This kidney stone is to be destroyed, or at least broken up.

Figure 1:
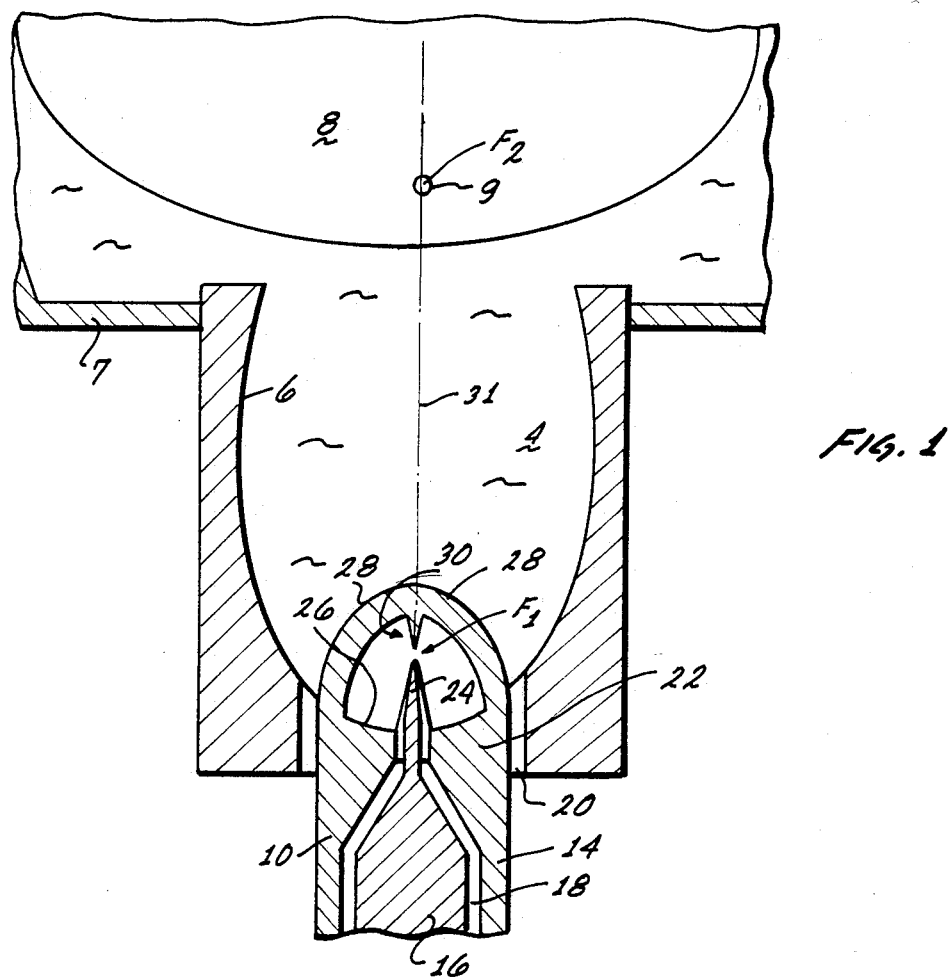
FIG. 1 is a somewhat schematic cross section through a device for the destruction of concrements in the body of a living being under utilization of a new and improved under water spark generator in accordance with the preferred embodiment of the invention.

The ellipsoid 2 is provided inherently with two focal points F1 and F2. The device is positioned in relation to the body 8 and here particularly to the concrement 9 such that that the concrement will be situated precisely in the focal point F2. The ellipsoid 2 is actually trunkated so that the focal point F2 is situated outside the chamber. An discharge path for a spark generator is situated in the focal point F1. This discharge path is a portion of the spark generator 10 to be described next.

The spark generator 10 includes the end portion of a pair of coaxial conductors, including in turn an outer conductor 14 and an inner conductor 16 being coaxially arranged to the outer conductor 14. The two conductors are separated by electrical insulation 18. The outer conductor is electrically insulated wherever needed, and in this case particularly in the portion adjacent the focusing chamber, there being electrical insulation 20 provided accordingly. This insulation moreover provides also for a certain attenuation.

The outer conductor 14 is configured near its end as a shaft portion 22 narrowing in fact its hollow interior. Accordingly, the end of inner conductor 16 tapers inside the shaft portion 22 and terminates in a pointed electrode 24, projecting beyond shaft portion 22. The tip or peak end of electrode 24 is closely situated to the focal point F1 of the ellipsoid 2. The two focal points F1 and F2 are aligned on the large axis of the ellipsoid.

The shaft portion 22 established a thicker and therefore mechanically stronger portion of the outer conductor 14 and is therefore provided as a strong support structure for a cage. The more (radially) inner portion of that outer conductor 14 is elliptically configured so that this particular end surface 26 is in effect a continuation of the ellipsoid within the spark and discharge generator.

A cage is established by means of arch shaped elements 28 extending from near the periphery of the outer conductor 16 at that surface 26. Upon comparing FIG. 1 with FIG. 2, it may be more correct to speak of semi-arch shaped elements as they end in the apex due to the three elements arrangement. Four pairwise aligned semi-arches would establish two arches, but three semi-arches suffice. These arches or semi-arches 28 loop around and reach over the focal point F1 and extend, so to speak, beyond the focal point F1 as far as the interior of the ellipsoid is concerned. These arches or semi-arches 28 carry the second electrode 30 which is likewise pointed. The two electrodes 30 and 24 are aligned along the large axis 31 of the ellipsoid 2.

Assuming that a sufficiently high voltage is applied to the two conductors 14 and 16, a spark discharges between the electrodes 24 and 30. This under-water spark generates a shock wave within the liquid 4, which propagates in all directions, but there is a pronounced transmission lobe in directions transverse to the main axis of the ellipsoid, particularly towards the wall 6. The transmitted shock wave is reflected at the curved wall 6 and focused into the second focal point F2. As a consequence, the concrement 9 will be destroyed, i.e., broken up into easily dischargeable and extractable pieces.

The coaxial arrangement of the spark generator meets a number of advantageous and important criteria. The several loop and arch elements 28 establish in effect a very low inductivity in the coaxial conductor and spark generating system. Contrary to the state of the art design, the cage diameter as established through these arches 28 can be quite large commensurate with the shaft 22, which is of course determined by the outer dimensions of the outer conductor 16. The elliptical configuration is defined by the long axis a, and in practical instances is about 125 mm., while the transverse axis b is about 75 mm. In such a case, one can provide a shaft end and (outer) conductor diameter of about 6 cm. This means that the arches 28 can be maintained sufficiently and consistently far from the inner electrode 24 so that even at operating voltages up to 30 kilovolts no parasitic discharge has to be expected, even if the arch elements themselves are not electrically insulated.

The inner diameter of this cage should, on the one hand not be made larger than necessary for reasons of reducing the inductance. This involves particularly the diameter dimension near the surface 26. On the other hand, the reduced inductivity in the electrode arrangement is the result of a cross-sectional enlargement of the coaxial conductor system as a whole.

The particular elliptical surface 26 of the electrode shaft 22 is made of a material which insures a high degree of reflection, particularly in the case of normal or near-normal incidence shock wave. A near normal direction and angle of incidence is indeed present at the surface 26. Brass was found to be highly suitable for this purpose. The electrode shaft 22 merges more or less transitionless with the ellipsoidal surface 6, because as stated, this shaft end surface 26 is in fact a portion of the reflector, and the insulation 20 between elements 2 and 22 is likewise contoured in accordance with the ellispoidal surface 6. Therefore, the efficiency of concentration and shock wave energy available for reflection and focusing is increased drastically.

It is conceivable that the outer conductor 14 is in fact electrically connected to the ellipsoid tube, and the shaft reflector 26 is then electrically insulated from the outer conductor 14, or is even made from insulating material. In this case of course the outer conductor 14 and the ellipsoid chamber 2 will be at the same potential which is expected to be ground.

Figure 2:
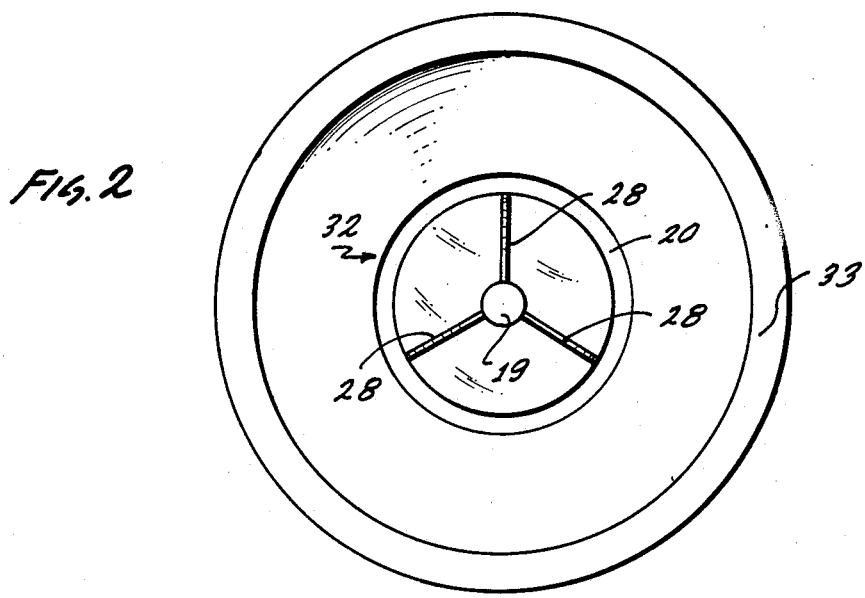
FIG. 2 illustrates a top elevation of the spark generator as shown in FIG. 1.

It can readily be seen particularly from FIG. 2 that the arches 28 are made from a flat shock, i.e., they have a flat configuration so as to extend physically primarily in 1 radial direction this feature is highly advantageous as compared with the known round rods for making a cage. A flat configuration particularly as far as the radial extension is concerned means that in axial direction there is minimum interference with the shock wave generation and propagation, particularly after reflection. On the other hand, the flat configuration as such, i.e., not too small a dimension in radial direction, as can be seen from FIG. 1, offers sufficient stability for the arrangement and construction.

Analagously to an electrical dipole the amplitude of the shock wave produced by a spark between the two axially oriented electrodes 24 and 30 varies with the azimuth angle, i.e., there are pronounced lobes of shock wave radiation. The largest amplitude is transmitted radially in the direction perpendicular to the axis between the two electrodes which, in this case, is made to coincide with the long axis of the ellipsoidal reflector configuration. The amplitude drops with angles shallower in relation to that ellipsoid axis.

The inventive electrode arrangement is chosen so that exactly that portion of the primary shock wave radiating away from the discharged area, and having the largest amplitude is in effect radiated towards the most important zones of the reflector as far as reflectance is concerned. This then ipso facto captures a very significant portion of the radiated shock wave without any interference. The very thin arches 28 minimize any residual interference as can be seen on a percentage basis as far as a full circumference is concerned (FIG. 2). A certain amount of the shock wave produced primarily is lost because it is not captured by the reflection which is a portion of the radiation radiating basically in up direction in FIG. 1. This portion is substantially lost, but as far as the power of creating shock waves is concerned, that portion is relatively minimal on account of the lobe structure of the radiating pattern.

If one compares the foregoing with the prior art manner of installing and mounting the discharge gap defining portions proper, one can see that in the prior arrangement a large portion of the principle lobe of the primary shock wave remained unfocused and was lost because it radiated directly out of the opening of the incomplete ellipsoid as defined by the chamber 2. The inventive structure avoides this loss and the amount of shock wave energy captured by reflecting portions in chamber 2 is considerably higher. The same can be said with regard to the radiation which is directed towards the ellipsoid apex which is in FIG. 1, the lower portion and identified by the shaft area 22. Even though that portion is comparatively low, the particular configuration is indeed amenable to capture even that residual radiation portion.

It can thus be seen that the disposition of the electrodes 24 and 30 in relation to, i.e., directly on the large axis 31 of the ellipsoid establishes a high degree of symmetry, which in turn enhances the reproduceability of the exact location for the spark discharge and of the focusing area of reflected energy! This then is a considerable improvement as compared with the prior art in which axial symmetry was not fully observed.

Turning briefly and in summary to the illustration of FIG. 2, one can see here the arch shaped elements 28 as seen from the ellipsoid opening. Within the ellipsoid 33, one can see the outer insulation 20 and the shaft portion 22 having of course the particular surface 26. There are provided three arch-shaped elements 28 and a holder 19 is provided near the apex of the arch configuration for the upper electrode 30 (FIG. 1). FIG. 2 does not illustrate the internal insulation and the configuration of the two coaxial electrodes 14 and 16; they are in fact covered by the arches, the holder 19, and the surface 26 of the upper shaft portion 22.

Figure 3:
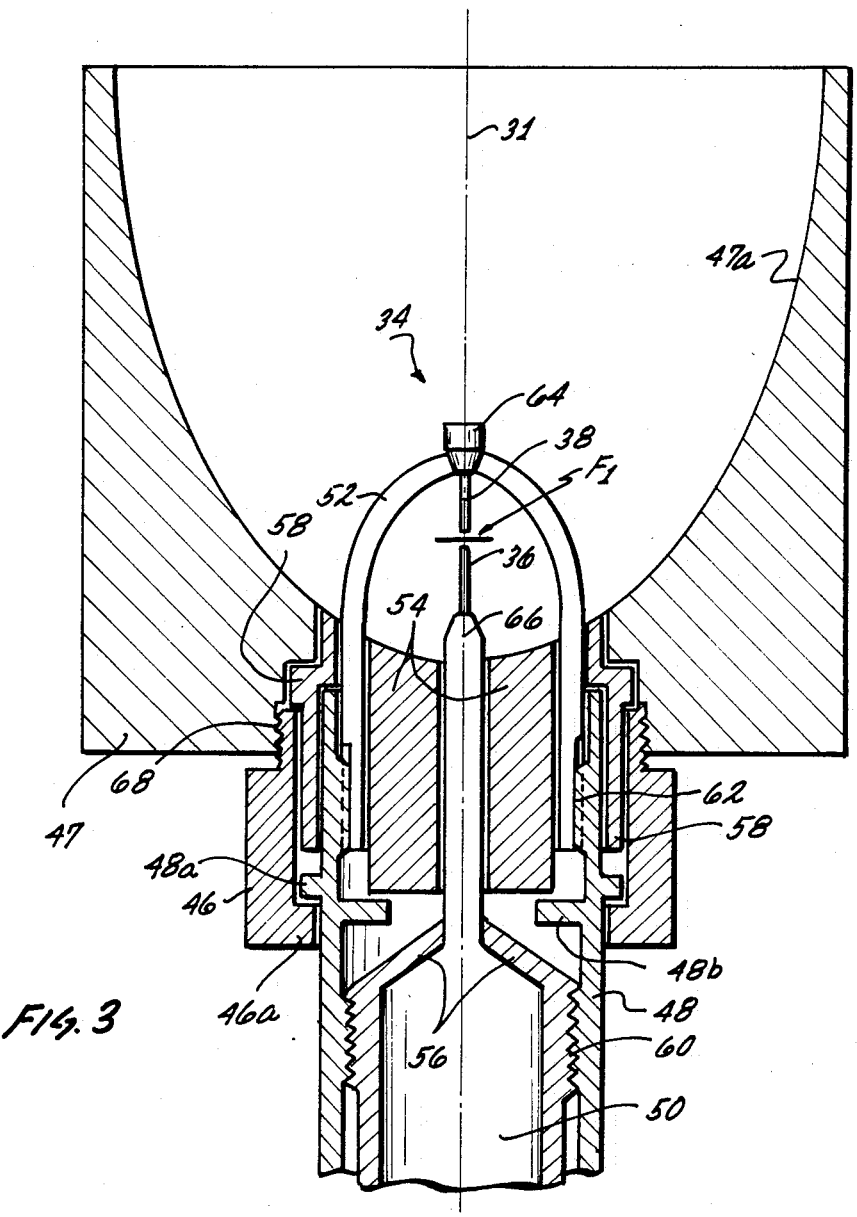
FIG. 3 illustrates an improvement and further detail for adjustable rod-like electrodes still constituting the preferred embodiment of the invention for practicing the best mode thereof.

Turning now to FIG. 3, there is illustrated an improved version for the electrode mounting and spark and shock wave generating facilities. The figure accordingly depicts a more complex spark generator 34 which, however, in this case is provided with a rapid exchange feature as well as with an adjusting feature for electrodes which are constructed as small rods 38 and 36. These rod like electrodes are coated with an insulation except for the respective tips facing each other. Adjustment devices which compensate for burn off of electrodes are known per se, so are clamping facilities for rapid action exchange of rodlike elements, such as fittings in drill equipment or the like. However, in the present configuration these features are structurally combined in a very advantageous manner. First of all, there is illustrated a sleeve 48 by means of which electrodes 36 and 38 can be moved in relation to each other and in coaxial fashion so that the discharge path proper between the tips of the electrodes will always include the primary or principal focal point F1 of the ellipsoid.

The particular arrangement illustrated is comprised of an outer conductor 48 and an inner conductor 50. A counter-clockwise threading 60 is provided by means of which a space sleeve 5-6 is threaded into the outer conductor 48 and is held in relation thereto in particular axial relationship. The outer conductor 48 in this case is therefore provided as a threaded sleeve. The inner conductor 50 is radially spaced and insulated from the inner conductor by the spacer sleeve 56.

The sleeve 48 moreover has a second but oppositely oriented threading 62, by means of which a electrode cage 52 is mounted and electrically connected to the outer conductor 48. The two threadings, 60 and 62, have opposite pitch.

The spark generator 34 is mounted to a reflector body 47, being of rotational paraellipsoidal configuration as far as its surface 47a is concerned. Mounting of the discharge generator 34 is carried out through an exchangeable sleeve 46 which has a ledge portion 46a engaging in annual rib 48a of the conductor 48. A threading 68 provides for the requisite connection of the sleeve 46 to the reflecting body 47.

The exchange and mounting sleeve 46 receives in nested configuration, a plurality of elements. These include of course primarily the outer conductor 48 as described, and the cage 52 for the electrode 38. The inner conductor 50 is separated generally from the outer conductor by the insulating sleeve 56 and, particularly in the area of the discharge path generator additional insulating sleeves 54, and 58 are provided. Herein insulating sleeve 54 is the principal mounting sleeve for the cage and arch elements 52. The sleeve 54 is penetrated by an electrode mount 66 on which is mounted one of the electrodes, electrode 36. The mount 66 is in effect the small diameter portion of an end portion of inner electrode 50. Reference numeral 56 is the primary insulating sleeve having a taper separating a holding ledge 48b for mount 54 from electrode 50.

The particuar sleeve 58 separates the outer conductor sleeve 48 from the mounting sleeve 46 in the upper part of both of them, and it separates also the cage 52 and its mounting structure 54 from the reflector body 47.

The cage 52 is constructed in a manner similar to the cage described earlier, and consists of flat arch shaped or semi arch shaped elements curving towards an apex in which is mounted a holder 64 for the electrode 38. The electrode 38 is held in holder 64 analogous to a drill or the like, in a bracketing mount with engaging jaws, and a clamping sleeve threaded thereon.

The adjustability of the structure is an adjustment of the two electrodes 38 and 36 in relation to each other; alter the electrodes 36 and 38 can readily be replaced on account of their mount in the holders 64 and 66 in similar fashion.

The outer conductor 48 when turned causes the inner conductor 50 with electrode 36 to be shifted in up or down directions, i.e., in particular relation toward or away from to the focus of F1, on the axis 31 of the ellipsoid. With the same rotation, but by operation of the opposite pitch threading 62, cage 52 will be lowered or raised so that electrode 38 is moved also towards or away from the focal point F1.

It can thus be seen that through a single turning moving of the sleeve 48, the conductor 50 with electrode holder 66 is shifted in one direction and the cage with holder 54 is shifted in the opposite direction. This operation will change the spacing of each of the electrodes 38 and 36 from the focal point F1 by same but oppositely directed amounts, which of course holds true for enlarging as well as for decreasing the spacing between the electrodes. The later point is not quite correct because the purpose of this arrangement is to make sure that the spark gap width can be made to remain constant in spite of electrode burnoff. The burnoff is simply compensated for by rotating the sleeve 48.

As can be seen particularly from FIG. 3, this adjusting feature is far as actuation is concerned, accessible from the outside. Therefore, focusing and efficiency as well as cavitation blowing can be optimized in the sense that previously optimized values can be retained and restored whenever necessary. This adjustment feature is shown generally to be manual, but it can readily be seen that automation can be introduced by causing the sleeve 48 to be rotated by automatic equipment.

As was outlined above, it is a particular object of the invention to permit also rapid exchange of electrodes in case they are no longer amenable to suitable adjustment, such as in case of irregular burnoff or simply they have burned off too much. This rapid action exchange is made possible by the mounts 64 and 66 holding the electrodes in chuck-like fashion. These elements 64 and 66 may be constructed with divided brackets and conical fastening nut so that all that is required is unthreading the sleeve 46 from the body 47 and taking the equipment out, unscrewing the fastening in the holders 64 and 66, and replacing the electrodes, whereupon the device can be reassembled. In this regard, it is quite significant that the neutral and initially attained adjustment of the parts 64 and 66 in relation to each other on account of the threaded mount at 60 and 62 is not disturbed. Certain trimming and fine tuning adjustment may be advisable, but the disassembly and reassembly of the electrode mounting and their replacement, etc., is not of the kind that interferes with the adjustment of these elements so that upon placing the electrodes into the holders 64 and 66, their mutual relationship is automatically restored once reassembly has been accomplished.

The invention is not limited to the embodiments described above, but all changes and modifications thereof not constituting departures from the spirit and scope of the invention are intended to be included.

We claim:

1. In an apparatus for destruction and breaking up of a concrement present in the body of a living being, and including an ellipsoidal reflector having two focal points, in one of the focal points is positioned a discharge path between two electrodes while the reflector is to be positioned such that the second focal point is situated in the location of the concrement to be destroyed, further including a pair of coaxial conductors for the application of high voltage to the electrodes, the improvement comprising:

first electrode means connected to an inner one of said coaxial conductors and positioned to extend towards said first focal point and extending particularly in the long axis of said ellipsoid;

a plurality of flat, arch-shaped or semi-arch shaped elements mounted on the outer one of said coaxial conductors and defining an arch apex;

means in said arch apex for mounting the second one of said electrodes, such that said second electrode extends also in said long axis and towards said first electrode;

said outer conductor, including shaft end means from which said arch or semi-arch shaped elements extend being penetrated by an end portion of said inner conductor and having a surface contour which merges with the ellipsoidal surface of said reflector; and means for coaxially moving said first and second electrodes in relation to each other.

2. The improvement as in claim 1 wherein said shaft end includes a brass portion or a material having similar reflective properties as far as incident shock wave is concerned.

3. The improvement as in claim 1 wherein said first electrode is mounted in a thinner extension of said inner conductor, the electrode being mounted and secured by releasably securing the first electrode thereto, said means for mounting said second electrode including release means for easy exchange of said second electrode.

4. The improvement as in claim 1 wherein said electrodes are thin cylindrical rods.

5. The improvement as in claim 4 wherein said rods are coated with insulation except for the tip.

6. In an apparatus for generating shock waves for purposes of contactless destruction and breakup of concrements in a living being comprising:

first means defining a truncated ellipsoidal reflector chamber having a first focal point situated within said chamber, and a second focal point located outside said chamber on account of said truncation;

a spark generator inserted in said chamber in a direction generally along the long and main axis of said ellipsoid in which the focal points are situated, said spark generator including a first conductor means continuing the outer one of a pair of coaxial conductors and having an end surface merging with and coinciding with said ellipsoidal reflector surface, there being arch shaped holding elements which extend from said surface;

said generator further including a first electrode mounted on the apex of said arch shaped holder to position a first electrode in the vicinity of said first focal point and extending generally along said main axis; and said generator further including a second electrode being the continuation of an inner one of said two coaxial conductors penetrating said shaft end and having an end oriented along and towards said axis for facing said first electrode.

7. The improvement as in claim 6 and including a threaded connection between said outer conductor and said holders for mounting said arched holders, and means providing a threaded connection between said inner conductor and said outer conductor such that upon turning said outer conductor said two electrodes are removed towards and/or away from each other, depending upon the direction of turning.

* * * * *